United States Patent [19]

Wohlgemuth

[11] 4,370,132
[45] Jan. 25, 1983

[54] ROTATABLE SOCKET FOR A DENTAL HANDPIECE

[75] Inventor: Juergen Wohlgemuth, Darmstadt, Fed. Rep. of Germany

[73] Assignee: Siemens Aktiengesellschaft, Berlin and Munich, Fed. Rep. of Germany

[21] Appl. No.: 248,863

[22] Filed: Mar. 30, 1981

[30] Foreign Application Priority Data

Mar. 28, 1980 [DE] Fed. Rep. of Germany ....... 3012152

[51] Int. Cl.³ .............................................. A61C 1/14
[52] U.S. Cl. ..................................... 433/128; 279/82
[58] Field of Search ................... 279/1 B, 76, 82, 93; 433/126, 128

[56] References Cited

U.S. PATENT DOCUMENTS

| | | | |
|---|---|---|---|
| 1,853,089 | 4/1932 | Skinner | 433/128 |
| 2,801,111 | 7/1957 | Kaltenbach | 433/128 |
| 2,895,738 | 7/1959 | Baker. | |
| 4,014,099 | 3/1977 | Bailey. | |

FOREIGN PATENT DOCUMENTS 2822708 12/1978 Fed. Rep. of Germany.

891672 12/1943 France.
1127453 9/1968 United Kingdom.

Primary Examiner—Robert Peshock
Attorney, Agent, or Firm—Hill, Van Santen, Steadman, Chiara & Simpson

[57] ABSTRACT

A rotatable socket for supporting a tool for rotation in a head housing of a dental handpiece. The socket includes a cylindrical or hollow tubular shaft for supporting a tool extending out of one end and having a dog for engaging a flattened surface on the shank of the tool for transmitting torque. To hold the tool in the socket, the socket has a catch device comprising at least one resilient element with a catch nose being disposed in the interior of the shaft to extend parallel to the axis of the shaft with the catch nose releasably engaging an annular groove in the shank of the tool. To disengage the tool, the catch device also includes a pressure element, which is disposed on the housing adjacent the free end of each resilient support element and which is urged into engagement with the free end of the support element to cause disengagement of each of the catch noses when a purchase has been actuated by pressure from the operator's thumb.

15 Claims, 9 Drawing Figures

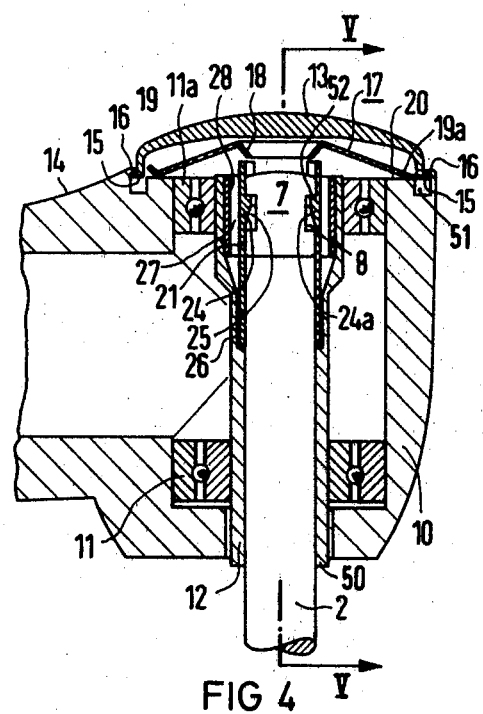
FIG 4
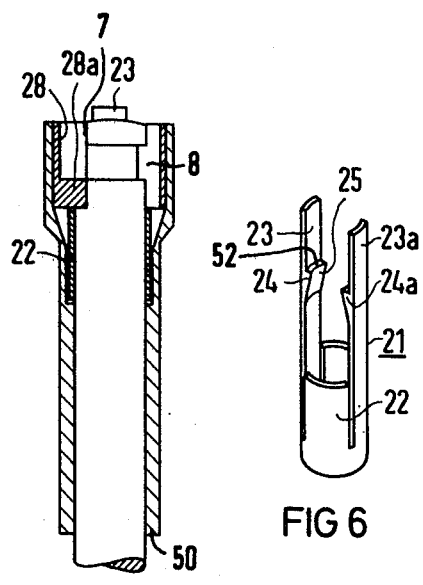
FIG 5
FIG 6
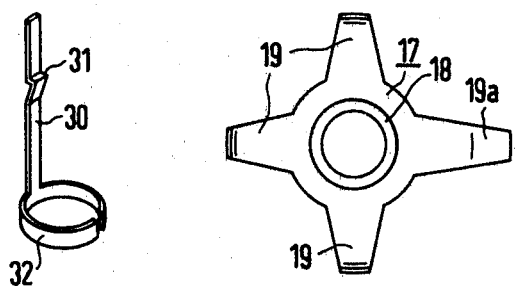
FIG 7
FIG 8
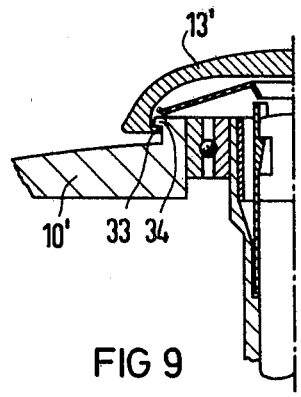
FIG 9

ROTATABLE SOCKET FOR A DENTAL HANDPIECE

BACKGROUND OF THE INVENTION

The present invention is directed to a socket for rotatably supporting a tool in a head housing of a dental handpiece. The socket includes a hollow cylindrical shaft which has a bore for receiving a tool which extends out of one end and has a dog for engagement with a flattened surface on a shank of the tool for transmission of torque therebetween. The socket has a catch means or device including at least one support element which extends parallel to the axis of the hollow cylindrical shaft and has a catch nose extending radially inward for engagement in an annular groove in the shank of the tool disposed in the shaft. The catch device includes a thumb actuated purchase disposed on the head housing for releasing each of the catch noses upon actuation to allow disengagement of the tool from the socket.

A known type of rotatable socket for rotatably supporting a tool in a head housing of dental handpiece is disclosed in British patent specification No. 1,127,453. In this tool, a tubular shaft receives the tool with it extending from one end and opposite that one end, an elongated support lamina or plate is movably mounted on the housing to engage a groove of the tool while in a locked position to prevent axial slippage of the tool from the tubular shaft. This support lamina is connected to a spring loaded slide which can be actuated by the thumb of the operator. For axial removal of the tool, the slide is actuated in a longitudinal direction so that the lamina is moved from the locking position to a released position. In this design, the slide must also be actuated when the tool is introduced into the hollow shaft. This arrangement of the slide, which is movable along the handpiece together with the support lamina represents a rather costly design which increases the size of both the head housing and the neck part of the handpiece. Moreover, constant friction exists between the rotating tool and the slide, which is fixed with respect thereto and therefore this friction will increase wear of both parts.

Another known design of a rotatable socket is disclosed in German O.S. No. 28 22 708. In this design, radially loaded clamping elements in the form of rotatable bodies, which have a concave surface of rotation, are provided for holding the tool in a locked position in a tubular shaft. The rotatable bodies are seated over a part of the circumference around the edges of an annular groove of the tool shank and are held in the locked position either constantly through a constant spring loading or by means of their self resiliency.

The space requirements for the rolling bodies likewise increases the size of the head housing particularly in the axial direction of the housing. If on the basis of work requirements, one proceeds from the fact that the head housing should be as short as possible and as small in diameter as possible, this type of structure would provide a relative small seating length and produce the disadvantage of less excellent bearing guidance for the tool which runs relatively fast. Since the full clamping force, which is required for only holding the tool, must be overcome for the axial removal of said tool, the force required for opening the clamping device, moreover, is relatively great in this design. A removal of the tool is thus only possible by means of a strong pull on the tool by hand or by utilizing a separate drill ejector, which must be inserted through an opening in the upper portion of the housing head. The force to be exerted in order to eject the tool must also be exerted in order to engage the tool.

Another known type of rotatable sockets is disclosed in U.S. Pat. No. 4,014,099. In this device, a hollow sleeve or tubular shaft, which accepts the tool, exhibits a catch nose at its upper end surface facing away from the tool discharge end of the hollow sleeve and the catch nose is engaged in an axial groove so that axial slippage of the tool is prevented. A further projection is provided in the sleeve for torque transmission between the tubular shaft and the tool; however, this projection does not engage the corresponding surfaces of the tool as the tool is inserted but rather only engages the tool when the tool is rotated with respect to the tubular shaft. For removal of the tool, the tool must first be rotated in the tubular shaft to align the tool. Then a specific axial force corresponding to the restraining force must be exerted on the tool to pull it out while the tubular shaft is held fast in order to prevent relative movement between the tubular shaft and the tool during the removal operation. Such requirements are also undesirable.

SUMMARY OF THE INVENTION

The present invention is to provide a rotatable socket which is improved in comparison to the prior art sockets in both terms of a tool support as well as its operations. Particularly the invention has the goal of being able to keep the head housing as compact as possible and as small in diameter as possible, even though ball bearings are employed for mounting the socket. In addition, the socket is to have the greatest possible bearing spacing available. Moreover, the tool should be supported largely friction free and be able to be placed in engagement and taken out of engagement within the socket without requiring the use of a great force.

This object is inventively achieved by an improvement in a rotatable socket for rotatably supporting a tool in a head housing of a dental handpiece, said socket including a hollow cylindrical shaft or tubular shaft having a bore for receiving a tool from one end and having a dog for engagement with a flattened surface of a shank of the tool for transmission of torque therebetween, said socket having a catch means comprising at least one support element extending parallel to the axis of said hollow cylindrical shaft and having a catch nose extending radially inward for engagement in an annular groove in the shank of the tool disposed in said hollow cylindrical shaft, said catch means including means biasing said catch nose radially inward and including a thumb actuated purchase disposed on the head housing for releasing each of the catch noses upon actuation to allow disengagement of the tool from the socket. The improvements comprise the hollow cylindrical shaft containing an inner recess, adjacent said bore for accepting the catch means, said recess receiving each support element and providing space adjacent the catch nose to enable radial outward movement of the catch nose to a position to enable disengagement of the catch nose from the tool, each support element being disposed in said recess, with a free end being adjacent the other end of the shaft and aligned with and disengaged from a pressure element disposed adjacent said other end of the shaft, said purchase being mounted on the housing and adjacent the pressure element for relative movement so that when actuated the purchase urges the pressure element into engagement with each free end of the support element to urge each of the catch noses radially outward to a position to release the tool in said socket. It should be noted that the purchase can be mounted to move in a tilting or pivotable movement or can be mounted to move along the axis of the shaft.

Significant advantages of the inventive design are that the rotatable socket is relatively simple to manufacture and assemble and that the support elements require relative little space particularly in diameter. Thus the head housing, particularly upon employment of ball bearings for the mounting of the tubular shaft accepting the tool, can be kept relatively small and the bearing length for the shaft can be optimally dimensioned.

Other advantages are also seen in its operation. In order to change the tool, brief pressure against the thumb actuatable purchase is sufficient and the type of actuation is largely up to the operator. He can actuate the purchase both by means of axial and/or by means of a lateral pressure. In particular, a combined pressing sliding motion such as a tumbling motion which is achieved by means by pressing with ones thumb obliquely from above onto the purchase with an acute angle to the neck part of the handpiece is particularly felicitious since it follows a natural posture of the hand and motion for the thumb. A further advantage is to be seen because the structure does not require any axial guidance to prevent canting during seating of the purchase.

BRIEF DESCRIPTION OF THE DRAWINGS

FIG. 4 is a cross-sectional view with portions in elevation of a rotatable socket in accordance with the present invention utilizing a different embodiment of the thumb actuated purchase;

FIG. 5 is a cross-sectional view with portions in elevation taken along lines V—V of the hollow shaft of the socket of the present invention;

FIG. 6 is a perspective view of one of the support elements utilized in the present invention;

FIG. 7 is a perspective view of another embodiment of a support element utilized in the present invention;

FIG. 8 is a plan view of a pressure element utilized in the present invention; and FIG. 9 is a partial cross-sectional view of the device of FIG. 4 utilizing another embodiment of the thumb actuated purchase.

DESCRIPTION OF THE PREFERRED EMBODIMENTS

Figure 1:
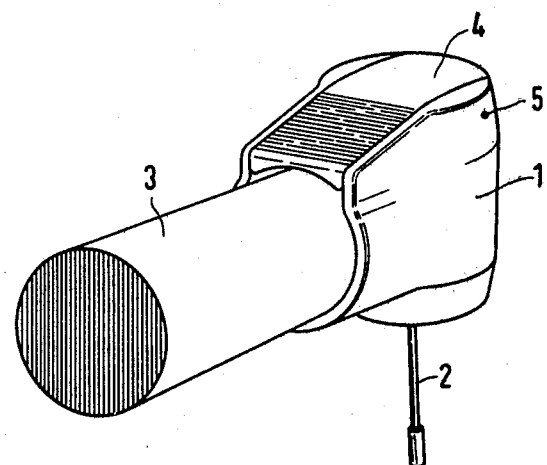
FIG. 1 is a perspective view of a head housing of a dental handpiece in accordance with the present invention.
Figure 2:
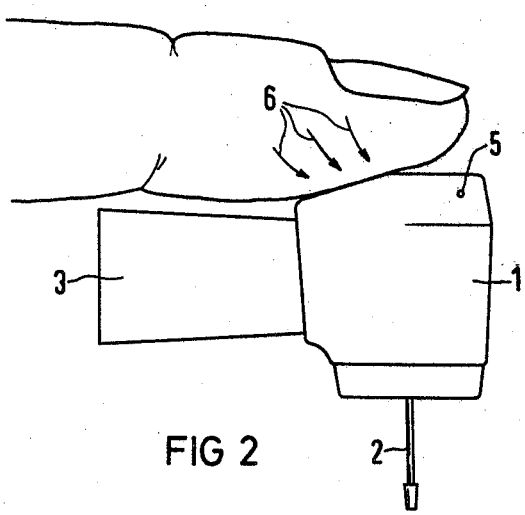
FIG. 2 is a side view of the head housing of FIG. 1.

The principles of the present invention are particularly useful when incorporated in a head housing 1 which has a rotatable socket for receiving a tool 2 which may be a drill, cutter, or bur. As illustrated in FIG. 1. the head housing 1 has a neck part 3, which will connect the housing to the remaining portions of a dental handpiece (not illustrated). On an upper portion of the housing 1 which is opposite the portion from which the dental tool 2 extends, a cover-like actuated purchase 4 is mounted to pivot or tilt around an axis or axle 5. As best illustrated in FIG. 2, the axle or bearing 5 is disposed in an upper part of the head housing and is at a portion of the head housing 1 which is opposite the neck part 3. The purchase 4 will tilt or pivot around the axle 5 when a pressure is placed thereon by a thumb of the operator which may either push downward in the direction of the axis of the tool 2 or push in a direction of the arrow 6 which pushing results in both a component directed along the axis of the tool 2 or a component transverse thereto. It is noted, that the movement of a thumb in the direction of arrow 6 corresponds to an actual posture and movement of the thumb when the handpiece or respectively the handpiece grip is grasped with the remaining fingers.

Figure 3:
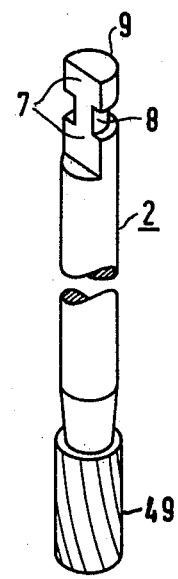
FIG. 3 is a perspective view of a tool which will be supported in the rotatable socket of the head housing of the present invention.

The tool 2, which is held in the rotatable socket of the present invention is best illustrated in FIG. 3. An end of the shank, which is opposite the cutting or working portion 49, has an annular groove 8 and a flat portion 7. As illustrated, the flat portion 7 intercepts the annular groove 8 and therefore removes a portion thereof.

The internal structure of the catch means for supporting a tool 2 in a rotatable socket of the present invention is illustrated in the embodiment of the head housing 10 which has a differently designed actuatable purchase 13. The rotatable socket includes a hollow-cylindrical shaft or tubular shaft 12 which accepts and receives a tool 2 with a portion extending out one end 50. The tubular shaft 12 is mounted for rotation in the head housing 10 by means of a pair of ball bearings 11 and 11a. On an upper end the head housing 10 has an annular groove 51 which is surrounded by an annular shaped inwardly directed flange 16. A cover type purchase 13, which has a shape to effectively merge with the contour of a neck portion 14 of the housing 10 acts as a cover and has a collar portion 15 which is received in the annular groove 51 and has an outwardly extending flange which is engaged under the flange 16. The cover purchase 13 can be pressed against or urged with its outwardly extending flange 15 engaged with the flange 16 by a resilient element 17, which has a star-shape.

The resilient pressure part 17, as best illustrated in FIG. 8, has a star-like configuration with a central formed part 18 as well as four support arms 19 whch extend therefrom. Of the four arms 19, a support arm 19a is slightly longer than the remaining three so that as best illustrated in FIG. 4, the support arms will lie on an upper surface or end face 20 of the housing 10 adjacent to the groove 51 with a portion of the support arm 19a extending under the peripheral edge 15 of the purchase 13 to form an abutment surface which allows the purchase 15 to move from a lateral actuation with a tilting or pivoting movement similar to the purchase 5 of FIG. 2. With the fixing of the resilient part 17 particularly against tilting, the centrally disposed part 18 forms a pressure element which has a conical shaped that is. aligned but out of contact with the end of the tube or shaft 12 and the support elements 21 which form part of the catch means for holding the tool 2 in the socket formed by the shaft 12.

The structure of the support element 21 is best illustrated in FIG. 6 and is a sleeve-like member having a base part 22, which is slotted to form a pair of diametrically opposite resilient tongues 23 and 23a. Each of the tongues is provided with a catch nose 24 and 24a which on one surface has a slanting surface 25 that extends up to a surface 52 which is best illustrated in FIG. 4 and is substantially in a plane extending perpendicular to the axis of the element 21 and the shaft 12. It should be noted, that the surfaces 52 match the surfaces forming part of the groove 8 on the shank of the tool 2.

To mount the support element 21, the tubular shaft 12 has an inner recess, which is concentric with the bore of the shaft and has a first portion 26 of increased diameter whose increased radius corresponds to the thickness of the support element 21 particularly at the base part 22. The recess extends into a second portion 27, which is substantially larger and which receives a sleeve-shaped dog 28 which is firmly received therein and has a projection or section 28a which rests against the flat surface 7 of the shank of the tool 2 and also coacts to prevent disengagement of the element 21 from the first portion 26.

In order to assemble the support element 21, the support element is inserted with play into the first portion 26. Subsequently the sleeve 28 is pressed into the second larger portion 27 so that the dog part or section 28a comes to lie between the two tongues 23 and 23a and to axially secure the support element 21 in the inner recess. In addition, it will prevent the tubular member 21 from rotating.

As best seen in FIG. 4, the two resilient tabs or tongues 23 and 23a essentially extend axially and parallel to the upper end of the head housing 2 and the tubular shaft 12. When the thumb actuated purchase 13 is actuated by means of pressing as illustrated in FIG. 2, then the centrally formed part 18 of the pressure element 17 comes into contact with the upper free ends of the two tongues. Due to its conical shape, the portion 18 will force the two tongues radially outward which is at right angles to the tool axis. With this movement of the tongues into the enlarged second portion 27, the catch noses 24 and 24a become disengaged from the annular groove 8 of the tool 2. Thus, the tool is easily removed from the head housing 10. After removal of the pressure against the purchase 13, the purchase will return due to the resilient pressure of the element 17 to its basic position in which the contact between the pressure element and the resilient tongues 23 and 23a is again eliminated. The inner recess as mentioned hereinabove, is dimensioned in such a manner that sufficient play remains for the excursion of the resilient tongues when they are spread apart.

With an insertion of the tool 2 into the shaft 12, the catch noses 24 and 24a of the resilient tongues 23 and 23a are pressed radially outward due to the end of the shank engaging the slanted surfaces 25. Then the tool is turned with respect to the shaft until the flattened surface 7 is aligned with the dog 28a, which is rigidly connected in the shaft 12. Upon further insertion, the noses 24 and 24a will finally be aligned with the annular groove 8 of the tool 2. In this position, they will move into a positive locking with the surfaces such as 52 engaging one of the surfaces forming the groove.

A different embodiment of the support element is illustrated in FIG. 7. Instead of two resilient tonges 23 and 23a as shown in FIG. 6, the element comprises a resilient ring 32 having a single resilient tongue or part 30 extending therefrom. As in the previous embodiment, the resilient part 30 will extend parallel to the axis and has a catch nose 31 which will be in the desired position when the ring portion 32 has been inserted into the first portion 26 of the recess.

Another type of seating for the thumb actuated purchase 13' is illustrated in FIG. 9. In contrast to the structure illustrated in FIG. 4, the cover 13' contains an inwardly directed flange 33 which overlaps an engages an outwardly extending flange or projection 34 on a head housing 10'. As in the previous embodiment illustrated in FIG. 4, it is up to the operator to determine how the purchase 13' or 13 will be actuated. Thus, by means of axial pressure from a thumb or by a lateral tilting movement. However, the actuation combining both a sliding and pressing as indicated by the arrow 6 in FIG. 2 will result in a type of a tumble type action which is particularly advantageous since this actuation largely corresponds to a natural hand posture and motion.

Although various minor modifications may be suggested by those versed in the art, it should be understood that I wish to embody within the scope of the patent granted hereon, all such modifications as reasonably and properly come within the scope of my contribution to the art.

I claim:

1. In a rotatable socket for supporting a tool for rotation in a head housing of a dental hand piece, said socket including a hollow cylindrical shaft having a bore for receiving a tool from one end and having a dog for engagement with a flattened surface on a shank of the tool for transmission of torque therebetween, said socket having a catch means comprising of at least one support element extending parallel to the axis of said hollow cylindrical shaft and having a catch nose extending radially inward for engagement in an annular groove in the shank of the tool disposed in said hollow cylindrical shaft, said catch means including means biasing said catch nose radially inward, said catch means including a thumb actuated purchase disposed on the head housing for releasing each of the catch noses upon actuation to allow disengagement of the tool from said socket, the improvements comprising the hollow cylindrical shaft containing an inner recess adjacent said bore for accepting the catch means, said recess receiving each support element and providing space adjacent the catch nose to enable radial outward movement of the catch nose to a position to enable disengagement of the catch nose from the tool, each support element being disposed in said recess with a free end being adjacent the other end of the shaft and a pressure element being disposed adjacent said other end of the shaft and in alignment with and disengaged from each free end, said purchase being mounted on the housing free of contact with all rotatable parts and adjacent the pressure element for relative movement so that when actuated the purchase urges the pressure element into engagement with each free end of the support element to urge each of the catch noses radially outward to a position to release a tool in said socket.

2. In a rotatable socket according to claim 1, wherein the pressure element comprises a resilient part having a centrally disposed portion for engaging each free end of the support element.

3. In a rotatable socket according to claim 2, wherein the resilient part has a plurality of support arms extending radially therefrom in a star-like manner, said support arms supporting said part on a surface of the housing with the centrally disposed part aligned coaxially with the hollow cylindrical shaft.

4. In a rotatable socket according to claim 3, wherein one of the support arms of the resilient part extends between the housing and a portion of the purchase to form a pivot point in which the purchase pivots during actuation.

5. In a rotatable socket according to claim 4, wherein the housing has a neck portion for connecting the housing to the rest of the dental handpiece, and said abutment is disposed on the head housing at a position lying opposite to the neck portion.

6. In a rotatable socket according to claim 1, wherein said inner recess has a first portion and a second portion, said first portion being concentric with the bore and having a radius larger than the radius of the bore by an amount corresponding to the thickness of the support element to enable receiving the support element with the free end extending into the second portion, said second portion having dimensions to enable the radial outward displacement of the free end to disengage the catch nose from the shank, said second portion receiving the dog for engagement with the flattened surface of the shank of the tool when inserted in the cylindrical shaft, said dog coacting to secure the support element in said first portion.

7. In a rotatable socket according to claim 6, wherein said support element comprises a ring portion inserted in the first portion and has at least one resilient arm supporting a catch nose extending axially therefrom into the second portion of the inner recess.

8. In a rotatable socket according to claim 7, wherein the support element has a single arm.

9. In a rotatable socket according to claim 7, wherein the support element has a pair of arms diametrically opposite to one another.

10. In a rotatable socket according to claim 6, wherein the second portion of the inner recess is disposed in an area adjacent the upper bearing supporting the hollow cylindrical shaft in said head housing, said upper bearing being opposite said one end.

11. In a rotatable socket according to claim 6, wherein the dog is disposed on an annular member which is firmly inserted in the second portion of said inner recess.

12. In a rotatable socket according to claim 11, wherein the support element comprises a sleeve-shaped member having a base part with at least one resilient tongue extending therefrom and parallel to the axis of said sleeve shaped member, said base part being inserted into the first portion of the inner recess with each resilient tongue extending into the second portion so that the catch nose disposed on each of the resilient tongues is positioned in the second portion of the recess.

13. In a rotatable socket according to claim 12, wherein the head housing has a neck part for connecting the head housing to the rest to the dental handpiece, said purchase being disposed on the head housing to rest against an abutment on an upper end of the head housing lying opposite to the neck part.

14. In a rotatable socket according to claim 1, wherein the head housing has a neck part for connecting the head housing to the rest of the dental handpiece, said purchase being disposed in the head housing to rest against an abutment on an upper end of the head housing lying opposite to the neck part.

15. In a rotatable socket according to claim 14, wherein the abutment is formed by a rigid bearing axle mounting the purchase for pivotable movement.

* * * * *